(12) United States Patent
Parthasaradhi et al.

(10) Patent No.: US 7,538,126 B2
(45) Date of Patent: May 26, 2009

(54) CRYSTALLINE FORMS OF VALDECOXIB

(75) Inventors: Reddy Bandi Parthasaradhi, Hyderabad (IN); Reddy Kura Rathnakar, Hyderabad (IN); Reddy Rapolu Raji, Hyderabad (IN); Reddy Dasari Muralidhara, Hyderabad (IN); Reddy Kesireddy Subadsh Chander, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 689 days.

(21) Appl. No.: 10/510,333

(22) PCT Filed: Apr. 4, 2003

(86) PCT No.: PCT/IN03/00139

§ 371 (c)(1),
(2), (4) Date: Oct. 5, 2004

(87) PCT Pub. No.: WO2004/087683

PCT Pub. Date: Oct. 14, 2004

(65) Prior Publication Data

US 2005/0143432 A1 Jun. 30, 2005

(51) Int. Cl.
A61K 31/42 (2006.01)
C07D 261/08 (2006.01)
(52) U.S. Cl. ..................................... 514/348; 548/247
(58) Field of Classification Search ................. 548/247; 514/348
See application file for complete search history.

(56) References Cited

U.S. PATENT DOCUMENTS

| 5,633,272 A | * | 5/1997 | Talley et al. ................ 514/378 |
| 5,859,257 A | | 1/1999 | Talley |

FOREIGN PATENT DOCUMENTS

| WO | WO 9625405 | 8/1996 |
| WO | WO 9806708 | 2/1998 |
| WO | WO-9806708 | * 2/1998 |

OTHER PUBLICATIONS

PCT International Search Report Dated Apr. 4, 2003.

* cited by examiner

*Primary Examiner*—Rei-Tsang Shiao
*Assistant Examiner*—Janet L Coppins
(74) *Attorney, Agent, or Firm*—Caesar, Rivise, Bernstein, Cohen & Pokotilow, Ltd.

(57) ABSTRACT

The present invention relates to novel crystalline forms of valdecoxib, to processes for their preparation and to pharmaceutical compositions containing them.

3 Claims, 3 Drawing Sheets

CRYSTALLINE FORMS OF VALDECOXIB

FIELD OF THE INVENTION

The present invention relates to novel crystalline forms of valdecoxib, to processes for their preparation and to pharmaceutical compositions containing them.

BACKGROUND OF THE INVENTION

Valdecoxib of formula (1):

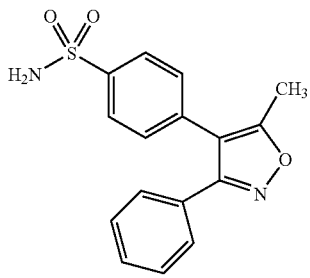

or 4-(5-Methyl-3-phenyl-4-isoxazolyl)benzenesulfonamide is a highly selective and potent cyclooxygenase-2 inhibitor in human whole blood and useful for the treatment of arthritis and pain. The therapeutic uses of valdecoxib are disclosed in WO 9625405.

Two novel forms of valdecoxib, form A and form B, are mentioned in WO 9806708.

We have discovered three stable novel crystalline forms of valdecoxib and these forms are found to be suitable for pharmaceutical preparations.

The object of the present invention is to provide stable novel crystalline forms of valdecoxib, processes for preparing these forms and pharmaceutical compositions containing them.

DETAILED DESCRIPTION OF THE INVENTION

In accordance with the present invention, there is provided a novel crystalline form of valdecoxib, designated as form I, characterized by an x-ray powder diffraction pattern having peaks expressed as 2θ at about 9.7, 13.1, 14.0, 14.5, 17.0, 17.1, 17.7, 19.4, 20.9, 21.3, 21.8, 24.1, 25.4, 26.3 and 29.1 degrees. FIG. 1 shows typical form I x-ray powder diffraction pattern.

In accordance with the present invention, a process is provided for preparation of valdecoxib form I. In this process, valdecoxib is dissolved in dimethyl formamide or N,N-dimethyl acetamide and valdecoxib form I is isolated from the solution. Valdecoxib in any crystalline form may be used. If valdecoxib form I is used in the process, its serves as a method of purification of valdecoxib form I. A mixture of dimethyl formamide and N,N-dimethyl acetamide; or dimethyl formamide or N,N-dimethyl acetamide mixed with any other solvent may be used. Valdecoxib form I can be isolated by the techniques like cooling, partial removal of the solvent or combination thereof. Crystallization may be initiated with the aid of seed crystals. Preferably, valdecoxib is mixed with dimethyl formamide or N,N-dimethyl acetamide and heated to about 50° C. to reflux temperature. The solution so formed is preferably maintained at 25° C. to 30° C. for 3 to 5 hours and the valdecoxib form I crystals formed are separated by filtration or centrifugation.

In accordance with the present invention, there is provided a novel crystalline form of valdecoxib, designated as form II, characterized by an x-ray powder diffraction pattern having peaks expressed as 2θ at about 12.2, 15.4, 15.9, 19.9, 20.6, 22.0, 23.0, 23.6, 23.9, 24.5, 25.1, 28.6 and 31.3 degrees. FIG. 2 shows typical form II x-ray powder diffraction pattern.

In accordance with the present invention, a process is provided for preparation of valdecoxib form II. In this process, valdecoxib is dissolved in acetonitrile and isolated valdecoxib form II from the solution. Valdecoxib in any crystalline form may be used. Preferably valdecoxib is dissolved in acetonitrile at about 40° C. to 45° C. and valdecoxib form II is separated at about 25° C.-30° C. The valdecoxib form II may be collected by filtration or centrifugation.

In accordance with the present invention, there is provided a novel crystalline form of valdecoxib, designated as form III, characterized by an x-ray powder diffraction pattern having peaks expressed as 2θ at about 11.6, 12.2, 12.9, 13.3, 15.4, 15.7, 16.7, 17.0, 17.4, 18.1, 19.7, 20.6, 21.9, 22.4, 23.1, 23.4, 23.8, 24.4, 25.3, 25.7, 26.1, 28.5 and 29.7 degrees. FIG. 3 shows typical form III x-ray powder diffraction pattern.

In accordance with the present invention, a process is provided for preparation of valdecoxib form III. In this process, valdecoxib is dissolved in an ester solvent and isolated valdecoxib form III from the solution. Preferably the solution is cooled to 5° C. to 30° C. to get the crystals of valdecoxib form III. The valdecoxib form III may be collected by filtration or centrifugation. Valdecoxib in any crystalline form may be used in the process. The suitable ester solvent is selected from n-butyl acetate, ethyl acetate, methyl acetate, isopropyl acetate, tert-butyl acetate, ethyl formate, methyl formate. A combination of the ester solvents may also be used.

In accordance with the present invention, there is provided a pharmaceutical composition comprising form I of valdecoxib and a pharmaceutically acceptable carrier or diluent.

In accordance with the present invention, there is provided a pharmaceutical composition comprising form II of valdecoxib and a pharmaceutically acceptable carrier or diluent.

In accordance with the present invention, there is provided a pharmaceutical composition comprising form III of valdecoxib and a pharmaceutically acceptable carrier or diluent.

Figure 1:
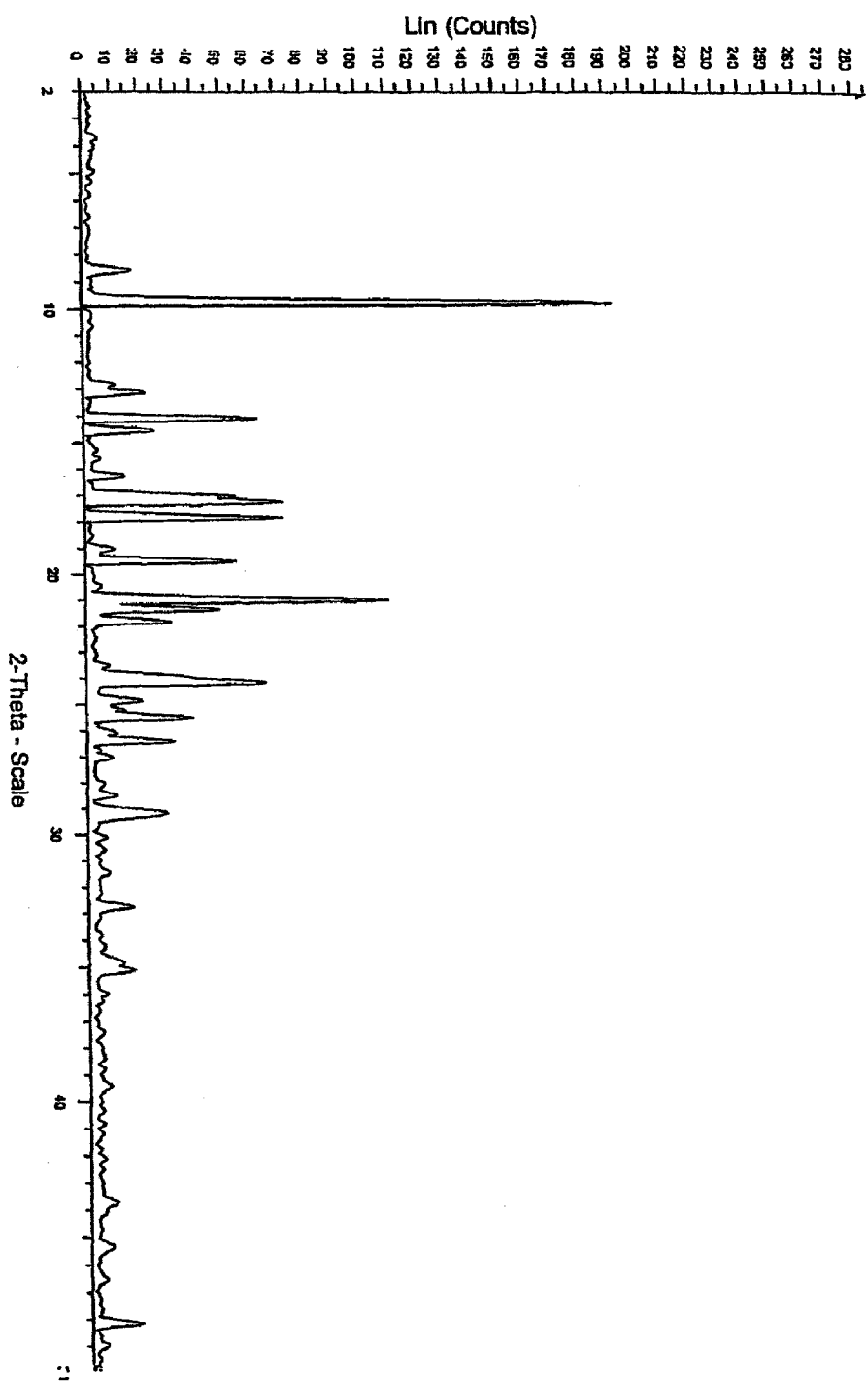
FIG. 1 is a x-ray powder diffraction spectrum of valdecoxib form I.
Figure 2:
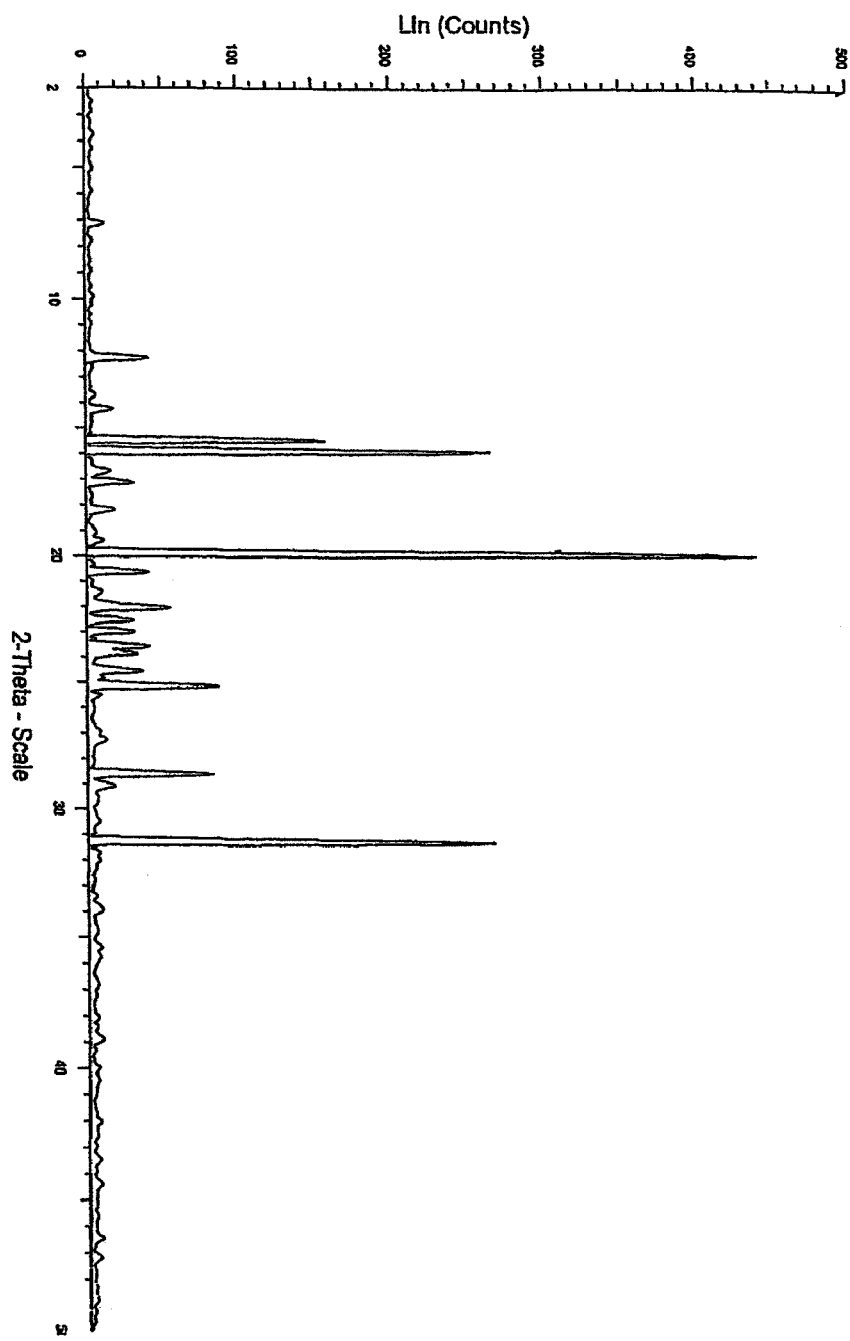
FIG. 2 is a x-ray powder diffraction spectrum of valdecoxib form II.
Figure 3:
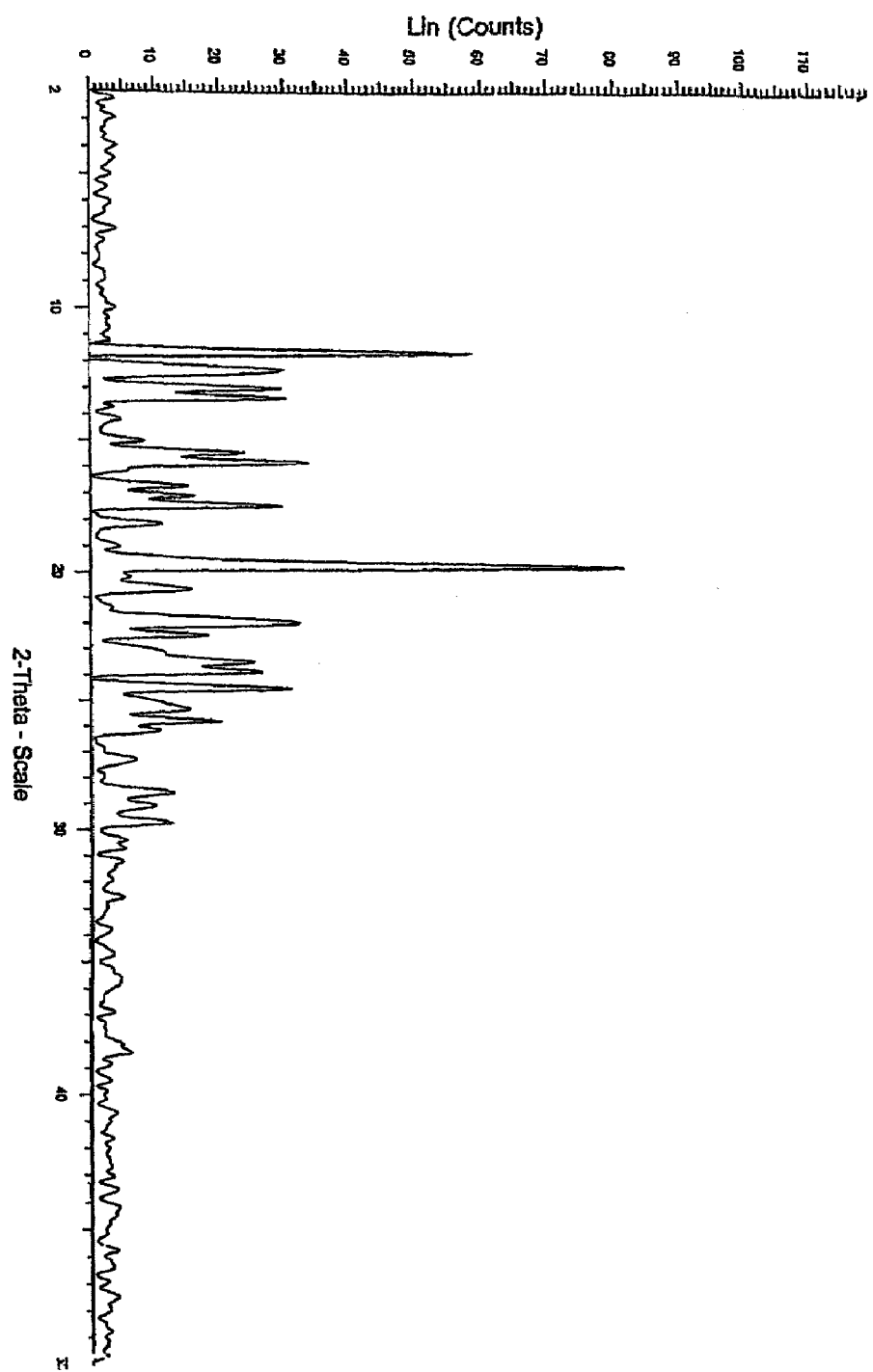
FIG. 3 is a x-ray powder diffraction spectrum of valdecoxib form III.

x-Ray powder diffraction spectrum was measured on a Siemens D5000 x-ray powder diffractometer having a copper-Kα radiation.

The following examples are given for the purpose of illustrating the present invention and should not be considered as limitations on the scope of spirit of the invention.

EXAMPLE 1

Valdecoxib (10 gm, obtained by the process described in example 1 of WO 9625405) is dissolved in dimethyl formamide (50 ml), heated to 50° C. and the solution obtained is cooled to 25° C. and maintained at 25° C. to 30° C. for 3 hours. The separated crystals are filtered to give 9 gm of valdecoxib form I.

EXAMPLE 2

Valdecoxib (10 gm) is dissolved in acetonitrile (125 ml), heated to 40° C. and the solution obtained is cooled to 25° C. and maintained at 25° C. to 30° C. for 6 hours. The separated crystals are filtered to give 9.5 gm of valdecoxib form II.

EXAMPLE 3

Example 1 is repeated using valdecoxib form II for valdecoxib to give valdecoxib form I.

EXAMPLE 4

Example 2 is repeated using valdecoxib form I for valdecoxib to give valdecoxib form II.

EXAMPLE 5

Valdecoxib (10 gm) is mixed with n-butyl acetate (100 ml), heated to 80° C. The solution so formed is cooled to 25° C. and maintained at about 25° C. for 5 hours. The separated crystals are filtered to give 8.5 gm of valdecoxib form III.

EXAMPLE 6

Example 5 is repeated using valdecoxib form II for valdecoxib to give valdecoxib form III.

We claim:

1. A crystalline valdecoxib form I, characterized by an x-ray powder diffraction pattern having peaks expressed as $2\theta$ at about 9.7, 13.1, 14.0, 14.5, 17.0, 17.1, 17.7, 19.4, 20.9, 21.3, 21.8, 24.1, 25.4, 26.3 and 29.1 degrees.

2. The crystalline valdecoxib form I as defined in claim 1, further characterized by an x-ray powder diffraction pattern as in FIG. 1.

3. The crystalline valdecoxib form I as defined in claim 1, further characterized by an x-ray powder diffraction pattern having peaks expressed as $2\theta$ at about 9.7, 13.1, 14.0, 14.5, 17.0, 17.1, 17.7, 19.4, 20.9, 21.3, 21.8, 24.1, 25.4, 26.3 and 29.1 degrees.

* * * * *